United States Patent [19]
Valkirs

[11] Patent Number: 5,914,241
[45] Date of Patent: Jun. 22, 1999

[54] ASSAYS AND KITS FOR DETECTING ANALYTES IN THE PRESENCE OF CROSS-REACTING SUBSTANCES

[75] Inventor: Gunars E. Valkirs, Escondido, Calif.

[73] Assignee: Biosite Diagnostics, Inc., San Diego, Calif.

[21] Appl. No.: 08/006,341

[22] Filed: Jan. 19, 1993

[51] Int. Cl.⁶ ........................ G01N 33/536; G01N 33/573
[52] U.S. Cl. ........................... 435/7.4; 435/7.5; 435/7.92; 435/17; 435/971; 436/518; 436/540
[58] Field of Search ................. 435/7.4, 7.5, 7.9, 435/7.92–7.95, 17, 21, 22, 962, 971, 975; 436/500, 518, 531, 540, 808, 819, 825

[56] References Cited

U.S. PATENT DOCUMENTS

| | | | |
|---|---|---|---|
| 4,376,110 | 3/1983 | David et al. | 436/513 |
| 4,486,530 | 12/1984 | David et al. | 435/7.9 |
| 4,740,468 | 4/1988 | Weng et al. | 435/7.1 |
| 4,912,033 | 3/1990 | Ladenson et al. | 435/7.4 |
| 4,945,043 | 7/1990 | Gerber | 435/7.4 |
| 5,026,653 | 6/1991 | Lee et al. | 436/518 |
| 5,155,022 | 10/1992 | Nagui et al. | 435/7.32 |
| 5,202,234 | 4/1993 | Shah et al. | 435/7.4 |

FOREIGN PATENT DOCUMENTS

| | | |
|---|---|---|
| 2084317 | 4/1982 | United Kingdom . |

OTHER PUBLICATIONS

Prager, N.A. et al J. Am Coll Cardiol 20:414–9 1992.

D. Armbruster, "The Genesis and Clinical Significance of Creatin Kinase Isoforms", Laboratory Medicine, vol. 22 No. 5 (May 1991) pp. 325–334.

The American Heritage Dictionary 2nd College Edition 1976 p. 703.

Puleo et al. (1990) Circulation 82 (3) :759–764.

*Primary Examiner*—James C. Housel
*Attorney, Agent, or Firm*—Townsend and Townsend and Crew LLP

[57] ABSTRACT

An immunoassay is provided which is selective for an analyte over immunologically related substances which may be present in a sample to be tested. The presence of the analyte is detected using a first binding substance, typically an antibody, in the presence of a second binding substance, typically another antibody. The first binding substance recognizes an epitope which is characteristic of the analyte and cross-reacts with a related epitope on the cross-binding substance. The second binding substance preferentially binds the common epitope on the cross-binding substance, thus reducing non-specific binding of the first binding substance.

14 Claims, 1 Drawing Sheet

FIG. 1

ASSAYS AND KITS FOR DETECTING ANALYTES IN THE PRESENCE OF CROSS-REACTING SUBSTANCES

BACKGROUND OF THE INVENTION

1. Field of the Invention

The present invention relates generally to methods for detecting target analytes in samples which may contain cross-reacting substances. More particularly, the present invention relates to immunoassays which minimize binding between a detecting antibody and the cross-reacting substance.

A wide variety of assay techniques exist for detecting the presence of a target analyte in a biological specimen. Of particular interest to the present invention, specific binding assays rely on detecting the analyte using a binding substance which reacts with the analyte in a highly selective manner. The use and specificity of such specific binding assays has been greatly enhanced by the availability of monoclonal antibodies. Monoclonal antibodies allow the performance of immunoassays which can detect particular epitope(s) on an analyte of interest in a highly specific manner.

The detection of certain analytes which are antigenically similar to other substances which may be present in a particular specimen, however, remains problematic. In some cases, it will be desirable to detect an analyte which differs only in a small region of the molecule when compared to other substances which may be present in the sample. For example, it will sometimes be necessary to distinguish between proteins which differ by as little as one amino acid in their sequences. Similarly, it may be necessary to distinguish between glycoproteins and carbohydrates which differ by as little as one sugar residue or in other very minor ways. In such cases, the availability of monoclonal antibodies which can distinguish between these very small differences is not assured.

One such instance involves the detection of creatine kinase isoenzymes which are released from tissue damaged as a result of acute myocardial infarction. It has been found that patients suffering chest pain and other symptoms of myocardial infarction who have inconclusive electrocardiograms may be diagnosed based on the presence of certain creatine kinase (CK) isoenzymes in their blood. While such CK isoenzymes are normally released in the blood as a result of muscle cell turnover, the amount of CK isoenzyme MB (CKMB) is substantially higher in the myocardium than in other muscle tissues. Thus, the release of CKMB in the blood is diagnostic of myocardial infarction.

Although conclusive in most instances, present CKMB assays require a post-symptom period of about six hours in order for diagnostically significant levels of CKMB to build up in the blood. Such a delay in diagnosis is usually unacceptable, particularly when the measurement is being performed in order to initiate and monitor certain thrombolytic therapies to open stenosed arteries.

CKMB measurement can provide a much more rapid diagnosis by specifically detecting certain isoforms of the enzyme. The CKMB isoenzyme exists in tissue as a dimer of the M subunit and B subunit, with each subunit having a carboxy terminal lysine. After release into blood, the lysines of both subunits of the tissue isoform are cleaved, with the tissue isoform having a half life of several hours.

It is thus possible to diagnose acute myocardial infarction based on the relative amounts of the tissue and blood isoforms of CKMB. That is, individuals having elevated levels of the tissue isoform relative to the blood isoform can be assumed to have recently suffered significant tissue damage. Since CKMB is found at high levels in the myocardium, such levels will confirm a diagnosis of myocardial infarction, particularly when combined with the other symptoms which occasioned the test in the first place.

For these reasons, it would be desirable to provide improved specific binding assays, particularly immunoassays, which are capable of distinguishing between closely related analytes. It would be particularly desirable if such assays could distinguish between proteins, glycoproteins, carbohydrates, and other large biomolecules, which differ from each other in only very small ways, such as by a single amino acid deletion or substitution in a protein. Such methods and assays would be useful for distinguishing between the tissue and blood isoforms of CKMB in the diagnoses of acute myocardial infarction.

2. Description of the Background Art

U.S. Pat. Nos. 4,376,110 and 4,486,530, describe immunometric assays which employ a monoclonal capture antibody and a monoclonal detection antibody. Similar assays are performed using polyclonal antibodies as either or both of the capture and detection antibodies. Assays for diagnosing myocardial infarction based on the measurement of CKMB isoforms are described in Puleot et al. (1990) Circulation 82:759–764. Antibodies capable of binding to the M subunit and the B subunit of CKMB are described in U.S. Pat. No. 4,912,033.

The full disclosure of each of the references is incorporated herein by reference.

SUMMARY OF THE INVENTION

Assays for determining the presence and/or amount of an analyte in a sample which may contain a cross-binding substance comprise reacting the sample with a first binding substance in the presence of a second binding substance. The first binding substance, typically an antibody, binds specifically to an epitope which is characteristic of the analyte, but also binds to an epitope on the cross-binding substance. The second binding substance, also typically an antibody, will bind to the epitope on the cross-binding substance and will thus be able to reduce binding of the first binding substance to the cross-binding substance. Usually, the affinity of the second binding substance for the epitope on the cross-binding substance is greater than the affinity of the first binding substance for the epitope, but this will not be necessary so long as the concentration of the second binding substance can be increased sufficiently to provide the desired preferential binding.

The present invention further comprises kits for performing assays for an analyte in a sample which may contain a cross-binding substance. The kit will include a first binding substance which specifically binds to the analyte but which also binds to an epitope on the cross-binding substance. A second binding substance is also provided which binds to the epitope of the cross-binding substance, wherein the binding affinity and amounts of the first and second binding substances are such that the second binding substance will inhibit binding of the first binding substance to the cross-binding substance when added to a detection phase. The kit will further include means for detecting binding of the first binding substance to the analyte after the sample has been exposed to both binding substances in the detection phase.

The assays and kits of the present invention are particularly useful for detecting and measuring analytes in the presence of closely related substances, such as protein isoforms, and the like. The ability to inhibit non-specific binding of an antibody or other binding substance to such cross-binding substances can improve the selectivity by a factor of at least 2:1, frequently by a factor of 5:1, and often by a factor of 10:1, or greater where selectivity is defined as the ratio of a specific signal produced to non-specific signals produced.

DESCRIPTION OP SPECIFIC EMBODIMENTS

A method and kit are provided for detecting the presence and/or amount of an analyte in a sample. Suitable samples include virtually any material, specimen, substance, or the like, which is liquid, which can be liquified, or which can be suspended in a liquid. The method and kit will find their greatest use with biological specimens such as blood, serum, plasma, urine, cerebral fluid, spinal fluid, ocular lens liquid (tears), saliva, sputum, semen, cervical mucus, scrapings, swab samples, and the like, which are frequently employed in the diagnosis and monitoring of disease and therapeutic treatments. In addition, uses may be found with industrial, environmental, and food samples, such as water, process streams, milk, meat, poultry, fish, conditioned media and the like. In certain circumstances, it may be desirable to pretreat the sample, such as by liquification, separation, solubilization, concentration, filtration, chemical treatment, or a combination thereof, in order to improve the compatibility of the sample with remaining steps of the assay, as described hereinafter. The selection and pretreatment of biological, industrial, and environmental samples prior to immunological testing is well known in the art and need not be described further.

The analyte to be detected may be virtually any compound, composition, aggregation, or other substance which may be detected by immunological or equivalent techniques. That is, the analyte, or a portion thereof, will be antigenic or haptenic defining at least one epitopic site, or will be a member of a naturally-occurring binding pair (e.g., carbohydrate and lectin, hormone and receptor, ligand and receptor, and the like). Analytes of particular interest include antigens, antibodies, proteins, glycoproteins, carbohydrates, macromolecules, toxins, bacteria, tumor markers, and the like, which define a plurality of epitopic sites and which may have closely homologous or otherwise related substances which may be present in the sample. Other analytes of interest include haptens, drugs, and other small molecules, which usually define only a single epitopic binding site, but which may also have closely related metabolites and other substances which can lead to inaccuracies in measurement. A non-exhaustive list of exemplary analytes is set forth in U.S. Pat. No. 4,366,241, at column 19, line 7 through column 26, line 42, the disclosure of which is incorporated herein by reference.

Samples according to the present invention may include, in addition to the analyte, a cross-binding substance which comprises an epitope which is closely related to an epitope on the analyte. Usually, the analyte and cross-binding substance will share a number of identical or substantially identical epitopic sites, differing only in one, two, or several epitopic sites. The differing epitopic site(s), however, may differ only slightly, making it difficult to obtain antibodies or other specific binding substances capable of differentiating between the analyte and the cross-binding substance. Often, in the case of protein and glycoprotein analytes, the analyte and cross-binding substance will differ only by several or fewer amino acids, frequently by only a single amino acid substitution or deletion. Use of the present invention, however, is not limited to such closely related analytes and cross-binding substances, and will instead extend to any assay where results can be improved by employing second binding substances, as described in more detail below.

The assay of the present invention comprises reacting the sample with a first binding substance in the presence of a second binding substance. The term "binding substance" as used herein is defined broadly to include macromolecular compounds having spatial and polar features which permit binding specifically to another compound. Binding substances useful in the present invention will be selected or prepared to specifically bind to the analyte (the "first" binding substances) and to a potentially cross-reactive epitope on the cross-binding substance (the "second" binding substances). Natural binding substances may be selected from natural specific binding pairs, including antigens and antibodies, lectins and carbohydrates, hormones and hormone receptors, enzymes and enzyme substrates, biotin and avidin, vitamins and vitamin binding proteins, complementary polynucleotide sequences, drugs and receptors, enzymes and reaction products, and the like. Biotin and avidin derivatives may also be used, including biotin analogs, streptavidin, and the like.

Most often, no known natural specific binding substance will exist and one will have to be prepared. For antigenic and haptenic analytes and cross-binding substances, antibodies may be prepared by well known techniques. In particular, antibodies, and more particularly monoclonal antibodies may be prepared by well known techniques involving the immunization of vertebrates with an immunogen comprising the epitopic site of interest.

The first binding substance will bind to an epitopic site which is characteristic of the analyte. That is, the epitopic site will distinguish the analyte from at least most other substances which may be present in the sample being tested. The epitopic site, however, will be similar to epitopic site(s) on at least one other substance, referred to as the cross-binding substance, which may be present in the sample. In some cases, two or more different cross-binding substances may be present, with the different cross-binding substances including identical or differing cross-binding epitopes.

The first binding substance will usually be selected or prepared to bind with the epitopic site on the analyte with an affinity greater than that for the corresponding epitopic site on the cross-binding substance. The assay of the present invention, however, makes it possible to employ first binding substances which bind to both the analyte and the cross-binding substance with substantially equal affinities, or even bind to the cross-binding substance with a greater affinity than to the analyte. Such enhanced selectivity is obtained through use of the second binding substance which preferentially binds to the common epitope on the cross-binding substance, thus blocking binding of the first binding substance.

The second binding substance will be selected or prepared to bind to the cross-reactive epitope on the cross-binding substance with an affinity greater than its affinity for the epitope on the analyte. The second binding substance is then combined with the first binding substance and the sample at a concentration such that it binds preferentially to the common epitope on the cross-binding substance relative to the first binding substance. Thus, first binding substance remains available to bind to the target epitopic site on the analyte.

Assays according to the present invention may be run by a variety of protocols, including competitive and non-competitive (sandwich) protocols, employing a wide variety of direct and indirect labeling systems. The assays will find their greatest use with non-competitive assays where a capture antibody or other binding substance is immobilized on a solid phase and utilized to extract analyte from the sample. A labelled second antibody or other binding substance is used together with the capture antibody or in a second step to detect the presence of the extracted analyte on the solid phase. Use of the second specific binding substance, according to the present invention, may be combined either in the first capture and extraction step, the second labeling step, or in both. Specific techniques for performing these assays are described in detail hereinafter.

Non-competitive assay protocols according to the present invention can also be run by adding a labelled binding substance specific for the analyte-first binding substance complex prior to separation of the complexes from the sample reaction mixture. Such assays could also be run in homogeneous formats, such as those described in U.S. Pat. No. 3,817,837 (EMIT® assays available from Syva Co., Palo Alto, Calif.), and the like. The full disclosure of U.S. Pat. No. 3,817,837, is incorporated herein by reference.

Detection will take place in a detection phase. In the case of homogeneous assays (where no separation step is required), the detection phase will be the initial reaction phase to which the first binding substance, second binding substance, and label are added (where detection of label is modulated by the presence of analyte in the sample. More usually, the detection phase will be produced by separation of the analyte-first binding substance complex from the reaction phase into a separate detection phase. Such assays where separation is required are referred to as heterogeneous and are described in much greater detail hereinafter.

The present invention will also be useful for performing competitive assay protocols where labelled analyte or analyte analog are introduced to the sample and compete with the analyte for binding with a binding substance specific for the analyte. A second specific binding substance according to the present invention may also be added to the sample in order to inhibit nonspecific binding of the first binding substance, as described in more detail hereinafter.

Labeling systems useful in the present invention include labeling substances which may be any compound, molecule, moiety, or the like, which can be bound to a binding substance so as to provide a detectable label in the assay protocol. Suitable labeling substances include, but are not limited to, enzymes, enzyme cofactors, enzyme inhibitors, radioisotopes, chemiluminescent compounds, chromophores, scintillants, and the like. Suitable labeling systems may also employ an intermediate binding substance, such as avidin or biotin, which is attached to the binding substance (in the case of non-competitive protocols) and which mediates binding of the label. Preferred labeling molecules will be those which can be observed visually, e.g. lumiphores, fluorophores, scintillants, and chemiluminescers, and those which mediate the formation of a product that can be observed visually, e.g., a dye. Lumiphores, fluorophores, and chemiluminescers may be visualized directly through spectroscopic means while enzyme reporter molecules usually require addition of a substrate to form a reaction product that will be visible on the solid phase and/or the liquid phase. Such labeling materials and methods are well known and amply described in the patent and scientific literature.

Two-site immunometric assays generally utilize two antibodies, each of which is in excess over the amount of target antigen (analyte) in the sample. The relatively high concentration of antibody specific for the antigen of interest increases the cross-reactivity of the antibody for highly homologous antigens. If, for example, the antibody exhibits an affinity constant for the target antigen of $10^9 M^{-1}$ and an affinity constant for the cross-reactive epitope on the highly homologous antigen of $10^7 M^{-1}$, and if the antibody is in excess over the amount of target antigen and highly homologous antigen, then the amount of highly homologous antigen (Ag) that is bound to the antibody for the target antigen is related to the concentration of the antibody by the following relationship $$K[Ab]=[AbAg]/[Ag]=\text{bound antigen/free antigen}$$

If, for example, the concentration of antibody is $10^{-7}M$, then the ratio of bound to free antigen at equilibrium is 1. If the highly homologous antigen and the target antigen are present at equivalent concentrations, then the assay will falsely elevate the concentration of the target antigen by approximately 50% due to the cross-reactivity with the highly homologous antigen. As a result of such conditions found in non-competitive immunoassays, antibodies exhibiting very high specificity for the target antigen are required to reduce the cross-reactivity with homologous antigens to an acceptable level. For highly homologous antigens, it may not be possible to find single antibodies that exhibit sufficient differences in affinity to assay one of the two antigens independent of the other. The search for antibodies with the necessary characteristics can be a long and unproductive process if the probability of finding such antibodies is extremely low.

If assays could be developed for highly homologous antigens without requiring antibodies as specific as those required by the assays of the prior art, then immunoassays would be feasible for highly homologous antigens that currently cannot be measured by immunoassay. The present invention describes the use of combinations of two or more monoclonal antibodies that reduce the antibody specificity requirements for each antibody directed to a target antigen and enable the assay of highly homologous antigens. In the example cited above where the conditions of the assay resulted in a 50% falsely elevated result due to cross-reactivity, the same antibody used at the same concentration will provide a substantially lower cross-reactivity if the teachings of the present invention are employed. The present invention supplements the antibody used in the prior art assay with another antibody or other specific binding substance which is directed toward the same epitopic site on the highly homologous antigen that is bound by the first antibody. If the affinity of the second antibody for the highly homologous antigen is $10^9 M^{-1}$ and its affinity for the target antigen is $10^7 M^{-1}$ and if the second antibody is employed in the assay in excess over the amounts of target and highly homologous antigen together with the first antibody and substantially equilibrium conditions are achieved before the measurement, then the first antibody binds to the target antigen almost exclusively because the second antibody binds to the cross-reactive site on the highly homologous antibody and prevents the first antibody from binding at the cross-reactive site. Only 1% of the highly homologous antigen is bound by the first antibody under these conditions.

The equilibrium expressions for the binding of the two antibodies to the highly homologous antigen are as follows $$K_1[Ab1]=[Ab1:Ag]/[Ag] \text{ and } K_2[Ab2]=[Ab2:Ag]/[Ag]$$

These expressions may be combined to obtain the ratio of highly homologous antigen bound to the first antibody compared to highly homologous antigen bound to the second antibody.

$$[Ab1:Ag]/[Ab2:Ag]=K_1[Ab1]/K_2[Ab2]$$

When the concentrations of the two antibodies are the same, the ratio is equal to the ratio of the two affinity constants for the highly homologous antigen which equates to 0.01 for the above example. A similar expression for the ratio of target antigen (TAg) bound to the first and second antibodies may be derived using the affinity constants of these antibodies, $K_{1T}$ and $K_{2T}$, for the target antigen.

$$[Ab1:TAg]/[Ab2:TAg]=K_{1T}[Ab1]/K_{2T}[Ab2]$$

When the antibody concentrations are equal as they are in this example, this ratio is 100 for the affinity constants given above. By using these two antibodies together in an assay for the target antigen, the cross-reactivity contributed by the binding of the first antibody to the highly homologous antigen was reduced to 1% of the concentration of the highly homologous antigen. This is in sharp contrast to the 50% cross-reactivity obtained with assays of the prior art which do not use a second antibody that binds the highly homologous antigen. Thus the present invention enables substantial improvement in the specificity of immunoassays without requiring extraordinarily specific antibodies.

Those skilled in the art will appreciate that the absolute affinities of the antibodies used in the present invention do not need to be determined in order to practice this invention. Assays can be developed by identifying antibodies that exhibit different affinities for the same two sites on the target antigen and the highly homologous antigen. If one antibody can block the binding of a second antibody to an antigen, then the two antibodies bind to the same site according to the present invention. Two antibodies that bind to the same site can be evaluated for their relative affinity to that site by incubating both antibodies together at known concentrations in excess over the concentration of the antigen present in the mixture, and after equilibrium has been substantially achieved, determining the amounts of the antigen bound to one antibody compared to the other antibody.

In order to separate the antibodies and bound antigen in two-site immunometric assays according to the present invention, at least one of the antibodies must be labelled for detection or labelled to enable its separation from the other antibody. For example, the antigen may be immobilized on a solid phase such as a microtiter plate well and one of the antibodies may be conjugated to an enzyme such as horseradish peroxidase or alkaline phosphatase. Methods for the conjugation of two proteins are well known to those skilled in the art (see, for example, Wong, *Chemistry of Protein Conjugation and Cross-Linking*, CRC Press, Inc., Boca Raton, Fla.). After equilibrium has been established, the unbound reagents are washed away and the amount of bound labelled antibody is determined. The affect of the unlabelled antibody concentration on the binding of the labelled antibody is determined to establish the relative affinities of the two antibodies for the antigen. Alternatively, both antibodies may be labelled with different enzymes and their concentrations may both be varied to determine their relative affinities for the antigen. Rather than labelling the antibodies for detection, the antibodies may be labelled for separation and the antigen may be labelled for detection. For example, one antibody may be labelled with a molecular tag such as a fluorophore or a peptide. Such labelling procedures may be carried out by conjugation to the oligosaccharide portion of the antibody molecule as described in O'Shannessy and Quarles (1987) J. Immunol. Meth. 99:153–161. Antibodies specific for each molecular tag may be used to extract the tagged antibody and any labelled antigen bound to it from the mixture for detection of the labelled antigen.

A preferred immunoextraction assay process of the present invention employs a first antibody that binds to a specific epitopic site on the target antigen with higher affinity than it exhibits for a second epitopic site on a highly homologous antigen and a second antibody that binds to the same epitopic site on the highly homologous antigen with higher affinity than the first antibody and exhibits lower affinity for the target antigenic site than the first antibody. The first and second antibodies are incubated with the sample suspected of containing the target antigen and highly homologous antigen for a sufficient period of time to achieve substantially equilibrium binding. The relative amounts of the two antibodies are empirically selected to maximize the ratio of target antigen bound to the first antibody relative to the second antibody and to minimize the ratio of highly homologous antigen bound to the first antibody relative to the second antibody. The amounts of first and second antibodies are further selected to be in excess over the amounts of target antigen and highly homologous antigen in the sample.

The first antibody must be immobilized on a solid phase or must be separable from the second antibody through the use of a molecular tag which can be bound by a receptor or intermediate binding substance. The receptor is then immobilized on a solid phase in order to facilitate the separation of the first antibody from the second antibody. Methods for the immobilization of antibodies and receptors are well known to those skilled in the art. For example, the first antibody may be immobilized by adsorption to latex particles or by covalent attachment to latex particles. Alternatively, the first antibody may be tagged with a small molecule such as biotin and either avidin or an antibody to biotin may be immobilized on latex to facilitate the separation of the first antibody from the second antibody by, for example, centrifugation. Following separation of the first antibody from the second and, if necessary, washing of the solid phase containing the immobilized first antibody, the amount of target antigen bound to the first antibody is determined by, for example, determining the enzyme activity bound to the first antibody if the target antigen is an enzyme. Immunoextraction assays require the detection of the target antigen without using an antibody labelled for detection. Representative target antigens that may be assayed by this process include creatine kinase isoenzymes and tissue-specific enzymes such as alkaline phosphatases. Multiple target antigens may be assayed in the same sample if specific antibodies are incubated with the sample and means are employed to separate each antibody directed to a target antigen from the other components of the reaction mixture.

A preferred two-site immunometric assay process of the present invention employs a first antibody that binds to a specific site on the target antigen with a higher affinity than it binds to a specific site on a highly homologous antigen and a second antibody that binds to the same site on the highly homologous antigen with higher affinity than the first antibody and exhibits lower affinity for the target antigenic site than the first antibody. The relative amounts of the two antibodies are empirically selected to maximize the ratio of target antigen bound to the first antibody relative to the second antibody and to minimize the ratio of highly homologous antigen bound to the first antibody relative to the second antibody. The amounts of first and second antibodies are further selected to be in excess over the amounts of target antigen and highly homologous antigen in the sample. The first antibody may either be labelled for detection or it may serve as the capture antibody in the assay process. If the first antibody is labelled for detection, then another antibody specific for a second site on the target antigen is used to capture the complex of target antigen and labelled first antibody so that the amount of target antigen may be determined. The capture antibody may be immobilized directly on a solid phase or it may be labelled with a molecular tag such as biotin which may be bound by an immobilized receptor such as avidin. If the first antibody is not labelled for detection, it may be used as the capture antibody and the antibody that binds the second site on the target antigen must be labelled for detection. The two antibodies that bind to the two sites on the target antigen are preferably monoclonal antibodies that bind independently as described in U.S. Pat. Nos. 4,486,530 and 4,376,110. The second antibody that binds with higher affinity than the first antibody to the same site on the highly homologous antigen may be unlabelled if its only function is to prevent the binding of the first antibody to the highly homologous antigen. The highly homologous antigen may be assayed at the same time as the target antigen if, for example, the second antibody is labelled with a molecular tag and the first antibody is labelled with a different molecular tag and labelled antibodies specific for sites on the two target antigens are used so that the complexes formed by the labelled antibody/antigen/tagged antibody may be individually captured by receptors specific for the tags so that the amount of each captured labelled antibody is related to the amount of its respective target antigen in the sample. In this case the highly homologous antigen is the target antigen of the second antibody. If the second antibody binds to the same site on the target antigen as the first antibody, the higher affinity of the first antibody for that site prevents the second antibody from binding to any significant extent after substantially equilibrium conditions have been achieved. Therefore the amounts of target antigen and highly homologous antigen may be determined in a sample. Assays that can determine the amounts of multiple, highly homologous antigens in a sample can be developed by using the teachings of this invention. Assays measuring multiple, highly homologous antigens in a sample can utilize a different molecular tag for each different kind of antibody so that capture of the antibody and specific antigens bound to it in a complex can be achieved using an immobilized receptor for the molecular tag. Specific peptide tags are particularly preferred for this purpose because diverse sequences are easily synthesized which are not homologous to known sequences in proteins found in samples so that cross-reactivity is minimized. Furthermore, monoclonal antibodies are easily produced with high affinity and specificity for these peptide molecular tags.

A preferred competitive assay process of the present invention employs a first antibody that binds to a specific site on the target antigen with a higher affinity than it binds to a specific site on a highly homologous antigen and a second antibody that binds to the same site on the highly homologous antigen with higher affinity than the first antibody and exhibits lower affinity for the target antigenic site than the first antibody. In competitive assay processes of the present invention, the first antibody is generally not used in excess over the amount of the target antigen in the reaction mixture and the second antibody is used in excess over the amount of highly homologous antigen in the sample. The first antibody can be labelled for detection or it can be immobilized or labelled with a molecular tag to enable separation from the components of the reaction mixture that are not bound to the first antibody as a result of the assay process. For example, a reaction mixture containing the first antibody labelled with a molecular tag, the sample, the second antibody, and a conjugate of the target antigen and an enzyme is incubated until the binding reactions achieve substantially equilibrium binding. The first antibody and any conjugate bound to it are separated by contacting the reaction mixture with the immobilized receptor for the molecular tag and washing away, if necessary, any components of the reaction mixture that are not bound to the first antibody. The enzymatic activity of either the bound or the free fraction is determined by adding an appropriate substrate and detecting the product of the enzymatic activity. Standards containing known amounts of the target antigen are used to calibrate the assay response as a function of the concentration of the target antigen. Target antigens such as cyclosporine A can be assayed using the present invention in samples containing highly homologous metabolites of the parent compound.

A preferred immunoassay protocol according to the present invention provides for the measurement of CKMB isoforms in a patient serum or blood sample. The sequence of conversion of the tissue isoform of CKMB (CKMB3) is that the lysine at the carboxyl terminus of the B subunit is cleaved by carboxypeptidase N to yield CKMB2 which is further altered to CKMB1 by cleavage of the lysine at the carboxyl terminal of the M subunit. In principle, a fourth isoform which has the M subunit without lysine at the carboxy terminus and the B subunit with lysine at the carboxy terminus should be present in samples but has not been detected by the methods currently employed. In order to determine the amount of CKMB3 in blood, an immunoassay must be able to differentiate CKMB3 from the other two isoforms without resulting in inaccurate determinations that are due to antibody cross-reactivity among these highly homologous antigens. The present invention enables the accurate determination of the amount of CKMB3 and the sum of CKMB2 and CKMB1 without the need to employ extraordinarily specific antibodies.

Antibodies preferred for performing an assay for CKMB isoforms according to the present invention include a first monoclonal antibody that exhibits high affinity for the B subunit of CKMB with lysine present at the carboxyl terminus and lower affinity for the B subunit of CKMB with lysine absent from the carboxyl terminus, a second monoclonal antibody that exhibits higher affinity than the first antibody for the B subunit of CKMB with lysine absent from the carboxyl terminus and lower affinity than the first antibody for the B subunit of CKMB with lysine present at the carboxyl terminus, a third monoclonal antibody that can bind to a site on all isoforms of CKMB when either of the first two antibodies is bound, and potentially a fourth monoclonal antibody that exhibits a higher affinity for a site including the carboxyl terminus of the M subunit of CKMB whether or not lysine is present at the carboxyl terminus.

The need for the fourth antibody is dependent on the affinities of the first and second antibodies for the M subunit of CKMB which exhibits substantial amino acid sequence homology with the B subunit. If either the first or the second antibody binds substantially to the M subunit under the conditions of the assay without the presence of the fourth antibody, then the accuracy of the CKMB isoform determination will be affected. The presence of the fourth antibody in the reaction mixture of antibody reagents and sample will substantially eliminate the binding of the first and second antibodies to the M subunit and will improve the specificity of the assay. The fourth antibody must also be selected so that the third antibody can bind to CKMB when the fourth antibody is also bound. The antibodies are preferably monoclonal antibodies to enable consistent manufacture of the assay with the restrictions imposed on the relative affinities of the antibodies for highly homologous antigenic sites. The third antibody is preferably directed to a site that encompasses parts of both the M and the B subunits so that its binding is not appreciably affected by the presence of CKMM in the sample. Such antibodies are described in U.S. Pat. No. 4,912,033.

The four monoclonal antibodies described above can be prepared by standard techniques used to develop monoclonal antibodies (see, Harlow and Lane, eds., *Antibodies: A Laboratory Manual*, Cold Spring Harbor Laboratory, Cold Spring Harbor, N.Y.). In order to insure that antibodies with the desired specificity are provided, immunogens are preferably selected to direct the specificity of the antibodies generated in mice toward the desired specificities. Three tissue isoenzymes of creatine kinase are preferably used for the primary immunizations of animals and subsequent booster immunizations, CKMM3, CKMB3, and CKBB. In order to maximize the probability of generating the first monoclonal antibody, mice immunized with CKBB are boosted intravenously for three consecutive days prior to sacrifice and fusion of spleen cells and myeloma cells according to the method described by Liu, et al. (1987) Clin. Toxic. 25:527–538.

The immunogen used to boost the mice during this three-day period is preferably a conjugate of peptides covalently linked to the surface of a carrier protein such as bovine serum albumin (BSA). The peptide sequence is preferably selected to be at least the last ten and most preferably the last 15 amino acid residues of the B subunit, LEQGQAIDDLVPAQK SEQ ID NO: 1. This peptide sequence can be synthesized by methods well-known to those skilled in the art with the inclusion of a cysteine residue at the amino terminus. The thiol group of the cysteine residue can be used to couple the peptide to the carrier protein using the heterobifunctional reagent SMCC (succinimidyl 4-(N-maleimidomethyl)cyclohexane-1-carboxylate). A high ratio of peptides linked per carrier molecule is desired to increase the probability of binding the immunogen to cell surface receptors and subsequent stimulation of antibody-producing cells.

In order to screen for antibodies produced by hybridomas resulting from these fusions, the antigens used for immunization can be immobilized on microtiter plates and hybridomas secreting specific antibodies to the immunogens can be selected by standard ELISA (enzyme-linked immunosorbent assay) methods. Further characterization of the first antibody candidates is necessary in order to determine the relative affinities of a particular antibody for the B subunit of CKMB with lysine relative to the B subunit of CKMB without lysine.

A particularly valuable screening assay method employs the pure isoforms CKMB3 and CKMB1. The CKMB1 isoform can be prepared from purified CKMB3 by digestion with carboxypeptidase. Similarly, the cross-reactivity of the antibody with CKMM3 and CKMM1 can be determined using an assay which incubates the antibody with a conjugate of CKMB3 and an enzyme, for example alkaline phosphatase and any unlabelled cross-reacting antigen. After substantially equilibrium binding conditions are achieved, a reagent comprising goat-anti-mouse Fc antibody adsorbed to latex is added to bind all of the mouse antibody in the reaction mixture along with any conjugate bound to the antibody and the latex is separated from the unbound conjugate by centrifugation. Either the bound fraction or the free fraction is analyzed for enzyme activity. The effect of unlabelled CKMB3 concentration on the binding of antibody to labelled CKMB3 is determined to establish a standard curve and known concentrations of CKMB1, CKMM3, or CKMM1 are assayed to determine their recovery relative to the standard curve which is a measure of their cross-reactivity relative to CKMB3. Antibodies with substantially greater affinity for CKMB3 relative to CKMB1, CKMM3, and CKMM1 are first antibody candidates that must be evaluated further in assays that include the second, third, potentially the fourth antibody if the cross-reactivity with CKMM isoforms is not negligible.

The second monoclonal antibody can be generated in a similar manner. The primary and booster immunizations can be with CKBB or preferably with CKBB that has been digested with carboxypeptidase. The final intravenous boosts prior to sacrifice of the mice are preferably performed using a peptide carrier protein conjugate where the peptide is the same as for the first antibody except that the lysine on the carboxy terminus is absent. Assays analogous to those discussed for the first antibody are performed to determine the affinity of the second antibody candidates for CKMB1 relative to CKMB3, CKMM3, and CKMM1.

The third monoclonal antibody can be generated in a similar manner by using CKMB3, CKMB2, or CKMB1 as the immunogen. The final intravenous boosts prior to sacrifice of the mice are preferably performed using any of these three immunogens or a mixture of all three. Assays analogous to those for the first antibody are performed to determine the antibody specificity. The third antibody should preferably bind CKMB3, CKMB2, and CKMB1 with similar affinity but should not bind either CKMM isoforms or CKBB substantially. The CKMB2 isoform can be produced by hybridization of CKMM3 and CKBB subunits that have been treated with carboxypeptidase as described in Prager, et. al., "Nature and Time Course of Generation of Isoforms of Creatine Kinase, MB Fraction In Vivo", Journal of the American College of Cardiology, Vol. 20 (1992), 414–419.

If necessary, the fourth monoclonal antibody can be generated by immunization of mice with CKMM3, CKMM2, or CKMM1. In order to produce antibodies that bind specifically to the carboxy terminii of the CKMM isoforms, the final intravenous boosts are preferably performed using a peptide carrier protein conjugate where the peptide is the last 10 to 15 amino acid residues of the M subunit, LEKGQSIDDMIPAQK SEQ ID NO: 2, with or without lysine at the carboxy terminus. As before, the peptides can be conjugated to a carrier protein such as BSA by synthesizing the peptides with cysteine at the amino terminus and using the heterobifunctional reagent SMCC to couple the peptides to the protein. Assays using a conjugate of one of the CKMM isoforms and an enzyme can be performed using known concentrations of one of the CKMM isoforms to determine a standard curve and determining the cross-reactivities of the antibody with the other CKMM isoforms and with the peptides from the carboxy terminus. If necessary, two antibodies can perform the function of the fourth antibody if one of the antibodies is specific for the M subunit without the lysine at the carboxy terminus and the second antibody is specific for the M subunit with the lysine at the carboxy terminus. Using two such antibodies, each tagged for separate capture on a solid phase, assays for the individual CKMB isoforms can be performed.

Once the antibodies have been generated and characterized, prospective antibody candidates can be evaluated empirically in the CKMB isoform assay of the present invention. The first antibody can be labelled with a molecular tag such as biotin and the second antibody can be labelled with a molecular tag such as fluorescein. Preferred molecular tags for such labelling are peptides where each different antibody is tagged with a different peptide. The labelling can be accomplished using the oligosaccharide portion of the antibody molecule so that the antibody affinity is not substantially changed. Receptors for the capture of these tagged antibodies, avidin and an antibody for fluorescein, are preferably immobilized in discrete zones on a solid phase in a device where each zone is capable of binding the tagged antibodies with pseudo-first-order kinetics as described in Valkirs et al. (1985) Clin. Chem. 31:1427–31. The third antibody can be conjugated to an enzyme using succinimidyl-4-(N-maileimidomethyl) cyclohexane (SMCC) to modify the enzyme and N-succinimidyl-3-(2-pyridyldithio) propionate (SPDP) to modify the antibody so that free thiols on the antibody can react with SMCC-enzyme to form conjugates. Alkaline phosphatase is a preferred enzyme because substrates for this enzyme can be converted to detectable products in proportion to the amount of enzyme present. The fourth antibody, if necessary, is used unlabelled.

According to the present invention, the product of the antibody affinity for its specific target antigen and the antibody concentration in the assay relative to similar (affinity)X(concentration) products for the other antibodies and the highly homologous antigens in the sample determines how the target antigens being assayed and the highly homologous antigens are bound by the antibodies when substantially equilibrium binding is achieved in the assay process. In order to optimize the concentrations of the four antibodies in reaction mixtures with the sample, assays are performed using the purified CKMB and CKMM isoforms spiked into serum or plasma samples to determine what antibody concentrations minimize cross-reactivity with highly homologous antigens that are not assay targets and maximize assay response to the target antigens. The assay reaction mixture comprises the four antibodies labelled with their respective tags or conjugated for detection as described together with the sample. The reaction mixture is incubated until substantially equilibrium binding conditions are achieved such that the fraction of each target antigen bound by its respective antibody does not substantially change after this period of time has elapsed. The reaction mixture is contacted with the solid phase containing the discrete zones for the binding of the tagged first and second antibodies. The amount of target antigen bound to each discrete zone is determined by washing the unbound reagents from the discrete zones and contacting the discrete zones with a substrate solution so that the amount of enzyme activity bound to the zone can be determined by detection of a product that absorbs light or emits fluorescence or luminescence at characteristic wavelengths in quantities related to the amount of target antigen bound. If the detectable product is proportional to the amount of enzyme present, then the measured signal is proportional to the concentrations of isoforms being captured at each zone.

Figure 1:
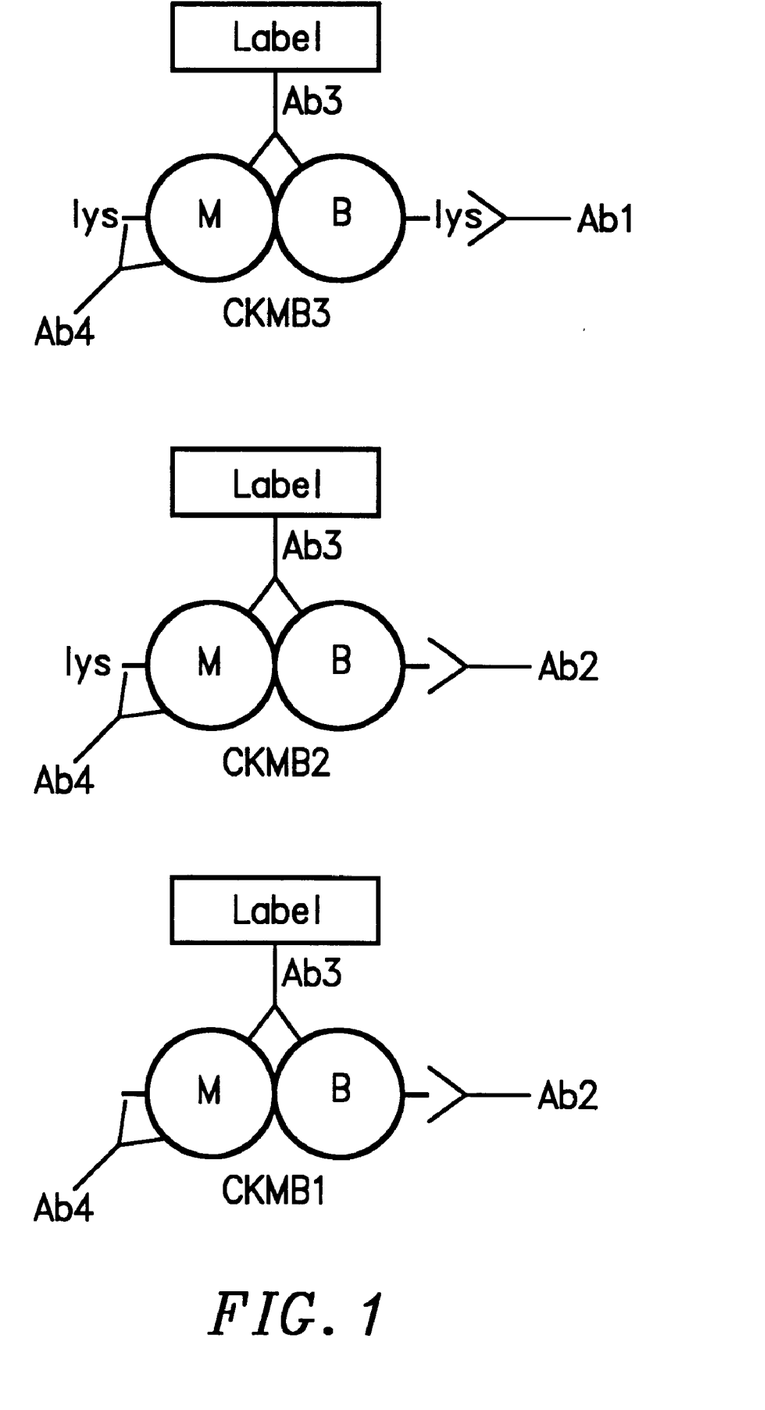
FIG. 1 shows complexes of antibodies and target antigens formed in a reaction mixture containing CKMB isoforms.

At the capture zones specific for the first and second antibodies, the measured signals are proportional to [CKMB3] and to [CKMB2]+[CKMB1] respectively. The two constants of proportionality that relate the measured signals to the isoform concentrations are determined for each lot of assay reagents by performing calibration assays using samples containing known concentrations of the isoforms. Such calibration enables the determination of [CKMB3] and [CKMB2]+[CKMB1] in samples as a result of the assay process and the ratio of [CKMB3]/[CKMB2]+[CKMB1] and the total [CKMB]=[CKMB3]+[CKMB2]+[CKMB1] can be calculated from the assay results. FIG. 1 depicts the complexes of antibodies and target antigens formed in a reaction mixture with sample containing the CKMB isoforms that are contacted with the solid phase. Separate solid phases each containing an immobilized receptor for one of the tagged antibodies can also be used to determine the isoform concentrations according to the present invention.

In the event that the individual concentrations of the CKMB isoforms need to be determined, a combination of antibodies can be used in assays to determine the individual isoform concentrations. The antibody combination includes a first antibody with higher affinity for the B subunit with lysine relative to the B subunit without lysine, a second antibody with higher affinity for the B subunit without lysine relative to the B subunit with lysine, and a third antibody specific for the MB isoenzyme without substantial cross-reactivity with CKMM or CKBB. The development of these three antibodies is already described in this example. The other two antibodies that are required are a fourth antibody that has higher affinity for the M subunit with lysine relative to the M subunit without lysine and a fifth antibody that has higher affinity for the M subunit without lysine relative to the M subunit with lysine. The fourth and fifth antibodies can be developed using methods described herein. The first, second, fourth, and fifth antibodies are preferably tagged with different molecular tags for capture on a solid phase using receptors for the molecular tags. These solid-phase capture receptors are either immobilized on separate solid phases or are immobilized in discrete zones on a solid phase so that the bound antibodies complexed with the CKMB isoform and the labelled antibody can be separately detected. The preferred molecular tags are peptides and the preferred receptors are monoclonal antibodies for the peptides. The third antibody is labelled for detection with, for example, an enzyme or a fluorescent molecule. A reaction mixture is formed which contains all five of the above antibody reagents together with the sample. The antibody concentrations are preferably selected such that each antibody concentration exceeds the concentration of its target ligand in the sample. The reaction mixture is incubated until the binding reactions achieve substantially equilibrium conditions and the reaction mixture is then contacted with a solid phase containing the capture receptors immobilized in discrete zones or portions of the reaction mixture are contacted with separate solid phases which each contain an immobilized receptor for one of the tagged antibodies. If the contact between reaction mixture and each immobilized capture receptor occurs in parallel so that no antibodies are bound by one receptor before contact is made with another receptor and the receptors do not compete for complexes containing more than one tagged antibody, then the immobilized receptor binds a representative fraction of the tagged antibody and complexes to which it is bound. Solid phase devices which contact the reaction mixture simultaneously and can contain immobilized receptors that do not compete for complexes containing more than one tagged antibody include those described in U.S. Pat. Nos. 4,632,901 and 4,727,019. Separate tubes or devices, each containing a different immobilized receptor for one of the tagged antibodies, can be contacted with portions of the reaction mixture so that a fraction of the tagged antibody and complexes to which it is bound are bound to the solid phase for detection. Following washing, if necessary, to remove unbound reagents, the signal detected from the bound labelled third antibody at each zone or in each device containing a single immobilized receptor is related to the concentration of the isoforms containing the tagged antibody bound by that receptor by a constant of proportionality if the immobilized receptor captures a constant fraction of the tagged antibody and if the signal is proportional to the amount of bound label over the assay range. If the fourth isoform of CKMB (CKMB4) containing the M subunit without lysine and the B subunit with lysine, is assumed to exist in samples, then the signal being measured at each receptor zone or in each device containing a single receptor is proportional to [CKMB3]+[CKMB4] for the first antibody receptor, [CKMB2]+[CKMB1] for the second antibody receptor, [CKMB3]+[CKMB2] for the fourth antibody receptor, and [CKMB1]+[CKMB4] for the fifth antibody receptor. The four constants of proportionality that relate the measured signals to the sums of isoform concentrations are determined for each lot of assay reagents by performing calibration assays using known concentrations of the isoforms in calibration samples. If the signal generating element is a calorimetric or fluorescent label that retains a constant response as a function of time and temperature, then the four constants of proportionality can be determined for a manufactured lot of assays for the life of the product by the manufacturer so that calibration by the user of the assay is unnecessary. If the signal generating element is an enzyme which acts upon a substrate to form a detectable product, then the signal is generally time and temperature dependent and the user must assay samples containing known concentrations of the isoforms in order to determine the four constants of proportionality that relate the measured signals to the sums of isoform concentrations. Knowledge of the four constants of proportionality and the measured responses at the four receptor zones for an unknown sample determines each isoform concentration exactly for that sample because the four isoform concentrations are four unknowns contained in four equations. If the [CKMB4] is zero for all samples because this isoform is not present in physiological samples, then one of the two equations containing [CKMB2] can be eliminated so that three equations in three unknowns remain with three constants of proportionality that need to be determined by calibration.

If the reaction mixture containing the sample and antibody reagents reaches substantially equilibrium binding conditions and is contacted with a solid phase where the receptors for tagged antibody are immobilized such that the reaction mixture is sequentially contacted with one immobilized receptor followed by another, then the concentrations of isoforms being determined at each immobilized receptor zone are simplified relative to the assay process where the reaction mixture contacts the zones in parallel. Preferred devices that provide sequential contact of a reaction mixture with more than one immobilized receptor include immunochromatographic devices such as those described in U.S. Pat. No. 4,740,468 and U.S. patent application Ser. No. 887,526. If three capture zones containing immobilized receptors for the tagged first antibody, the tagged fourth antibody, and the tagged second or fifth antibody are arranged in sequence on such devices and the reaction mixture is sequentially contacted with the zones in the above order and if the capture of each tagged antibody by its immobilized receptor is complete so that no tagged antibody travels past its respective capture zone, then the signal generated at the first zone is proportional to [CKMB3]+[CKMB4], the signal generated at the second zone is proportional [CKMB2], and the signal generated at the third zone is proportional to [CKMB1]. The constants of proportionality are determined by calibration as previously described. If the CKMB4 isoform does not exist in physiological samples, then the signal at the first zone is directly proportional to [CKMB3] and the concentrations of the isoforms in a sample are determined directly from the signals at the three zones.

In addition to the CK isoenzyme MB, an isoenzyme MM is released following acute myocardial infarction. The CKMM isoenzyme is present in myocardial tissue and in other muscle tissue to the same extent so that the assay of CKMM is far less specific than the assay of CKMB for the diagnosis of myocardial infarction. However, three isoforms of CKMM are found in blood. The tissue isoform that is first released is a dimer of two M subunits both of which contain a lysine at the carboxyl terminus. Carboxypeptidase N cleaves the lysine from one of the subunits to form the second isoform and cleavage of the lysine from the other M subunit of the dimer generates the third isoform. The tissue isoform of CKMM is processed to the two other isoforms relatively rapidly so that the ratio of the tissue isoform (CKMM3) to the fully processed isoform (CKMM1) has been determined by electrophoresis to be a early indicator of muscle damage, but is not specific for the diagnosis of AMI. However, with the advent of therapeutic agents such as the thrombolytics streptokinase and TPA, the need to monitor the success or failure of these procedures has become important in the management of patients subjected to thrombolytic therapy. When a diagnosis of AMI has already been determined prior to thrombolytic therapy, the lack of muscle specificity of the CKMM isoforms is not a practical limitation for their use in the determination of success of reperfusion. The CKMB isoform assay, of course, can also be used for this purpose. The best assay for the monitoring of the success of reperfusion will likely be an assay that detects the increase in the amount of the tissue isoform of either CKMB or CKMM relative to the amounts of the related isoforms in plasma. The immunoassays of the prior art do not satisfy this need.

An assay for CKMM isoforms can be similarly developed by producing a first antibody that exhibits high affinity for the carboxy terminus of CKM3 and lower affinity for the carboxy terminus of CKMM1, a second antibody with higher affinity than the first antibody for the carboxy terminus of CKMM1 and lower affinity than the first antibody for the carboxy terminus of CKMM3, a third antibody that is specific for CKMM isoform dimers and does not substantially cross-react with CKMB isoforms or CKBB, and a fourth antibody, if necessary, that has higher affinity for the carboxy terminus of the B subunit in CKMB isoforms or CKBB than either the first or the second antibodies. The antibodies are preferably all monoclonal antibodies and can be selected and labelled by methods already described. In an assay where two discrete zones are contacted in parallel with the reaction mixture in order to capture of the tagged first and second antibodies, the signals measured at the zones are proportional to [CKMM3]+[CKMM2] and [CKMM1]+

[CKMM2]. If an immunochromatographic device is used where the reaction mixture is first contacted with a zone for the capture of the tagged second antibody such that substantially all of the tagged second antibody is removed from the reaction mixture, and then with a zone for the capture of the first antibody, the response of the first capture zone will be proportional to [CKMM1]+[CKMM2] and the response of the second capture zone will be proportional to [CKMM3]. The constants of proportionality are determined by calibration using samples containing known isoform concentrations. Ratios of isoform concentrations and total [CKMM] can be calculated from the assay results.

Although the foregoing invention has been described in some detail by way of illustration and example, for purposes of clarity of understanding, it will be obvious that certain changes and modifications may be practiced within the scope of the appended claims.

plexes including the label, CKMB3, and first molecular tag and second complexes including the label, CKMB1 or CKMB2, and second molecular tag are formed;

contacting the reaction mixture after equilibrium has been reached with a first solid phase zone having immobilized receptor for the first molecular tag and a second solid phase zone having immobilized receptor for the second molecular tag; and detecting label bound within the first solid phase zone as a measure of the amount of CKMB3 in the sample and label bound within the second solid phase zone as a measure of the combined amounts of CKMB1 and CKMB2 in the sample.

2. An assay as in claim 1, wherein each molecular tag is selected from the group consisting of peptides, fluorescein, and biotin and the receptor is selected from the group consisting of antibodies to the peptides, antibodies to fluorescein, and avidin, respectively.

What is claimed is:

1. An assay for detecting CKMB1, CKMB2, and CKMB3 isoforms in a blood sample, said assay comprising:

reacting the sample in a liquid phase reaction mixture with (1) a first monoclonal antibody which binds to the B subunit of CKMB with lysine present and with a lower affinity to the B subunit with lysine absent, wherein the first monoclonal antibody is bound to a first molecular tag, (2) a second monoclonal antibody that binds to the B subunit of CKMB with lysine absent with an affinity greater than that of the first monoclonal antibody, wherein the second monoclonal antibody is bound to a second molecular tag, and (3) a third monoclonal antibody bound to a detectable label that binds to all three CKMB isoforms so that first com- 3. An assay as in claim 1, wherein the detectable label comprises an enzyme and detecting label comprises exposing each solid phase zone to substrate that is converted by the enzyme to a detectable product.

4. An assay as in claim 1, wherein the solid phase zones are located on a single solid phase.

5. An assay as in claim 4, wherein the solid phase zones are arranged in parallel.

6. An assay as in claim 4, wherein the solid phase zones are arranged in series.

7. An assay as in claim 1, wherein the solid phase zones are on separate solid phases.

8. An assay for detecting CKMB1, CKMB2, and CKMB3 isoforms in a blood sample, said assay comprising:

reacting the sample in a liquid phase reaction mixture with (1) a first monoclonal antibody which binds to the B subunit of CKMB with lysine and with a lower affinity to the B subunit without lysine, wherein the first monoclonal antibody is bound to a first molecular tag, (2) a second monoclonal antibody which binds to the B subunit without lysine and with lower affinity to the B subunit with lysine, wherein the second monoclonal antibody is bound to a second molecular tag, (3) a third monoclonal antibody bound to a detectable label which binds to the MB isozyme without substantial cross-reactivity with CKMM or CKBB, (4) a fourth monoclonal antibody which binds to the M subunit of CKMB with lysine and with lower affinity to the M subunit without lysine, wherein the fourth monoclonal antibody is bound to a fourth molecular tag, and (5) a fifth monoclonal antibody which binds to the M subunit of CKMB without lysine and with lower affinity to the M subunit with lysine, wherein the fifth monoclonal antibody is bound to a fifth molecular tag;

contacting the reaction mixture after equilibrium has been reached with a first solid phase zone having immobilized receptor for the first molecular tag, a fifth solid phase zone having immobilized receptor for the fifth molecular tag, and at least one of a second solid phase zone having immobilized receptor for the second molecular tag and a fourth solid phase zone having immobilized receptor for the fourth molecular tag; and detecting label bound within the first solid phase zone as a measure of the amount of CKMB3 in the sample, label bound within the fifth reaction zone as a measure of CKMB1, and label bound said within at least one of the second solid phase zone and the fourth solid phase zone to permit calculation of the amount of CKMB2.

9. An assay as in claim 8, wherein each molecular tag is selected from the group consisting of peptides, fluorescein, and biotin and the receptor is selected from the group consisting of antibodies to the peptides, to fluorescein antibodies, and avidin, respectively.

10. An assay as in claim 8, wherein the detectable label comprises an enzyme and detecting label comprises exposing each solid phase zone to substrate that is converted by the enzyme to a detectable product.

11. An assay as in claim 8, wherein the solid phase zones are located on a single solid phase.

12. An assay as in claim 11, wherein the solid phase zones are arranged in parallel.

13. An assay as in claim 11, wherein the solid phase zones are arranged in series.

14. An assay as in claim 8, wherein the solid phase zones are on separate solid phases.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 15 amino acids
      (B) TYPE: amino acid
      (C) STRANDEDNESS: single
      (D) TOPOLOGY: linear    (ii) MOLECULE TYPE: peptide    (xi) SEQUENCE DESCRIPTION: SEQ ID NO:1:

Leu Glu Gln Gly Gln Ala Ile Asp Asp Leu Val Pro Pro Gln Lys
   1             5                  10              15

(2) INFORMATION FOR SEQ ID NO:2:

(i) SEQUENCE CHARACTERISTICS:
      (A) LENGTH: 15 amino acids
      (B) TYPE: amino acid
      (C) STRANDEDNESS: single
      (D) TOPOLOGY: linear    (ii) MOLECULE TYPE: peptide    (xi) SEQUENCE DESCRIPTION: SEQ ID NO:2:

Leu Glu Lys Gly Gln Ser Ile Asp Asp Met Ile Pro Ala Gln Lys
   1             5                  10              15